United States Patent [19]

Orr et al.

[11] Patent Number: 5,074,146
[45] Date of Patent: Dec. 24, 1991

[54] GAS COMPARISON PYCNOMETER

[75] Inventors: Clyde Orr, Dunwoody; Ronnie W. Camp, Duluth; Kathryn H. Gibson, Stone Mountain, all of Ga.

[73] Assignee: Micromeritics Instrument Corporation, Norcross, Ga.

[21] Appl. No.: 438,752

[22] Filed: Nov. 17, 1989

[51] Int. Cl.[5] .............................................. G01N 9/26
[52] U.S. Cl. .......................................... 73/149; 73/37
[58] Field of Search .................................... 73/37, 149

[56] References Cited

U.S. PATENT DOCUMENTS

| | | | |
|---|---|---|---|
| 1,885,926 | 11/1932 | Lewis | 73/290 B |
| 3,060,724 | 10/1962 | Smith | 73/149 |
| 3,113,448 | 12/1963 | Hardway | 73/149 |
| 3,255,122 | 6/1966 | Constabaris | 73/38 |
| 3,788,125 | 1/1974 | Kirschstein et al. | 73/32 R |
| 4,083,228 | 9/1978 | Turner | 73/149 |
| 4,112,738 | 9/1978 | Turner | 73/149 |
| 4,239,623 | 12/1980 | Schrenker | 73/61.1 C |
| 4,527,418 | 7/1985 | Acara | 73/32 R |
| 4,763,518 | 8/1988 | Daviaud et al. | 73/1 H |

OTHER PUBLICATIONS

"Model 6102—Gas Comparison Pycnometer", Systems, Science and Software, May 1978—1980—at Pittsburgh Conference.
"A Microprocessor Controlled Gas Pycnometer" by Ronnie Camp, Charles Capehart and Clyde Orr, pp. 1-9.
"Micromeritics—AutoPycnometer 1320", Micromeritics Corporation.
H. M. Rootare et al., "Effect of Adsorbed Water on Sample Surface in Density Measurement with an Automatic Helium Pycnometer", Abstract, Pittsburgh Conference, 1981, No. 908.
Ronnie W. Camp et al., "A Microprocessor Controlled Gas Pycnometer", Abstract, Pittsburgh Conference, 1980, No. 288.
"Multi Volume Pycnometer 1305", Micromeritics Corporation.
"Instruction Manual Multivolume Pycnometer 1305", Jan. 23, 1987.
Shibata Brochure Analysis prepared for Micromeritics Instrument Corporation, "Surface Area Apparatuses, Type ASA-2000", pp. 1-7.

Primary Examiner—Hezron E. Williams
Assistant Examiner—Craig Miller
Attorney, Agent, or Firm—Jones, Askew & Lunsford

[57] ABSTRACT

A gas comparison pycnometer is disclosed which provides a method and apparatus for determining and checking the accuracy of the volume of a solid substance. The pycnometer is also outfitted with a unique cap assembly which fixes the volume in the pycnometer's sample chamber from run to run. The pycnometer also employs a series of purges with a suitable gas to carry unwanted moisture and vapors out of the system. This pycnometer solves many problems in the prior art by quickly and accurately determining the volume of a solid substance.

29 Claims, 11 Drawing Sheets

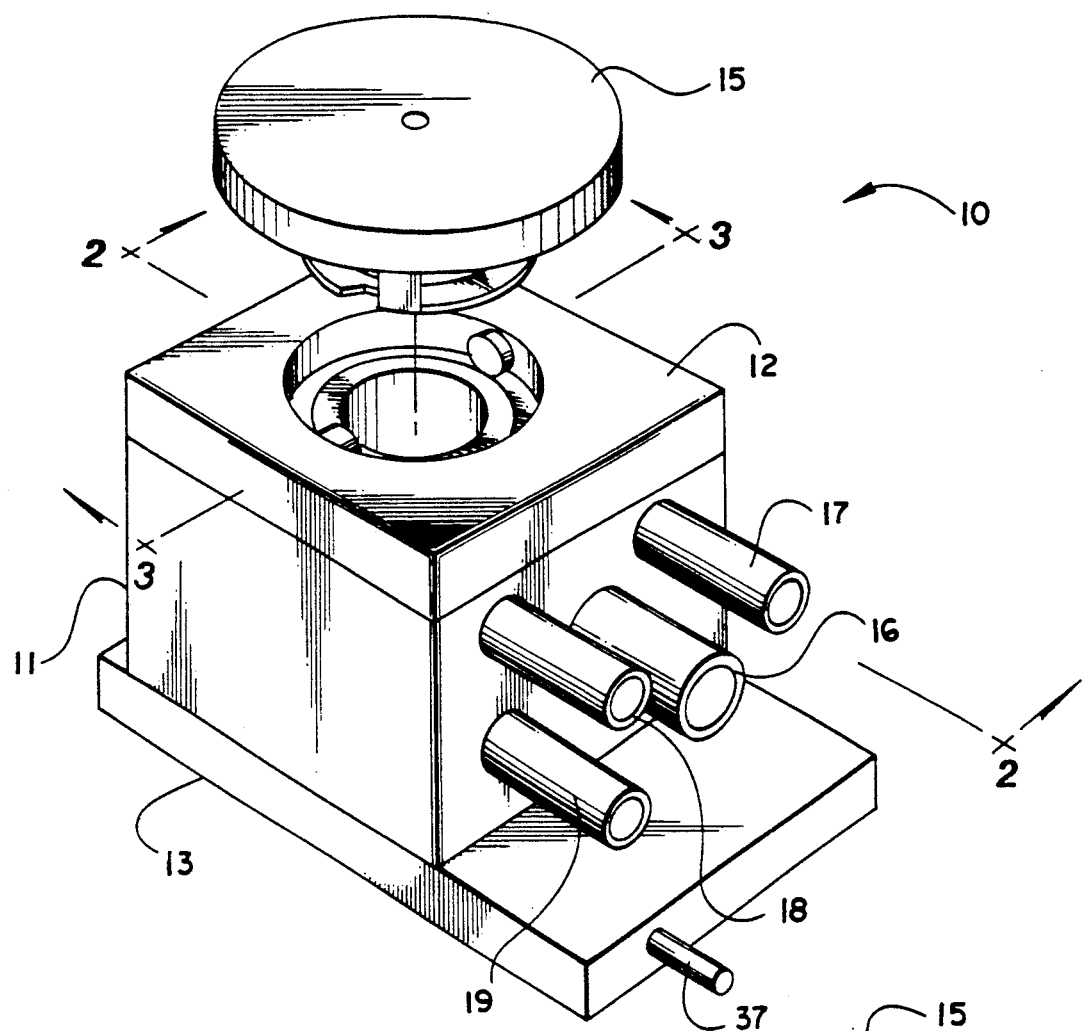
Fig_1
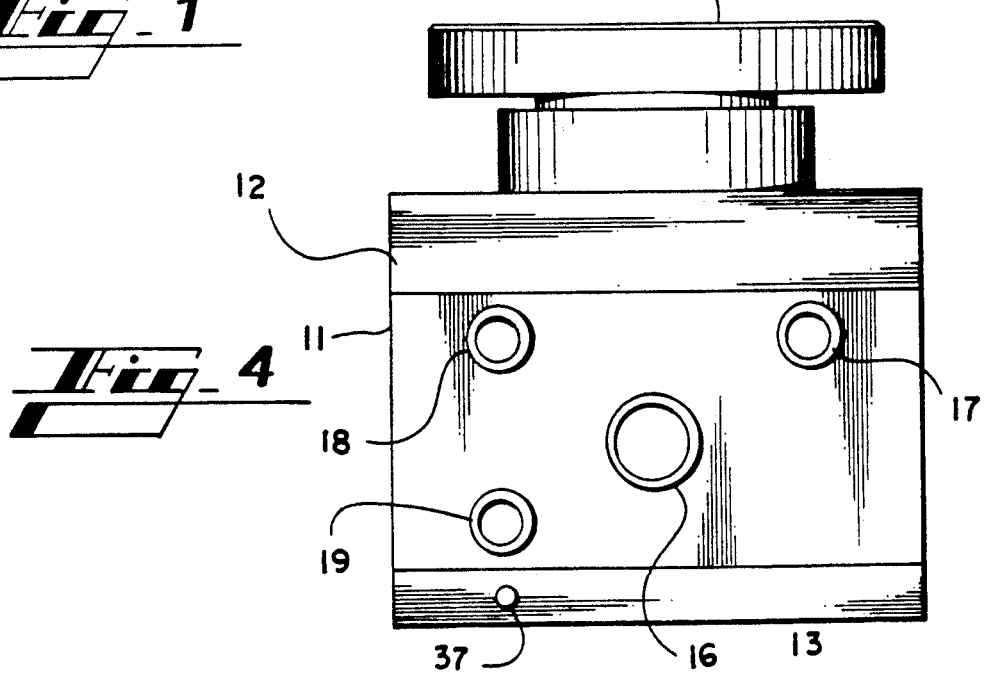
Fig_4

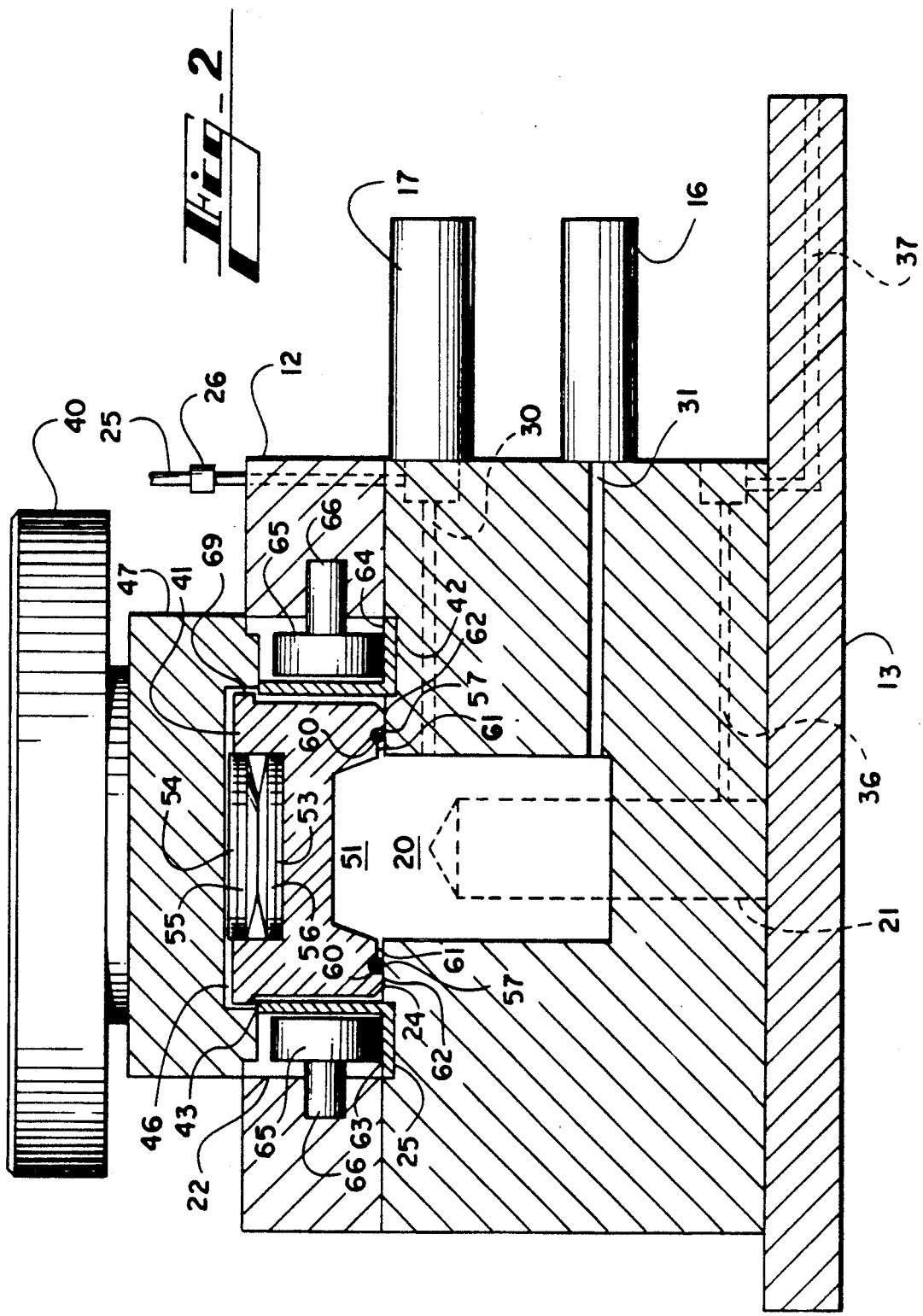

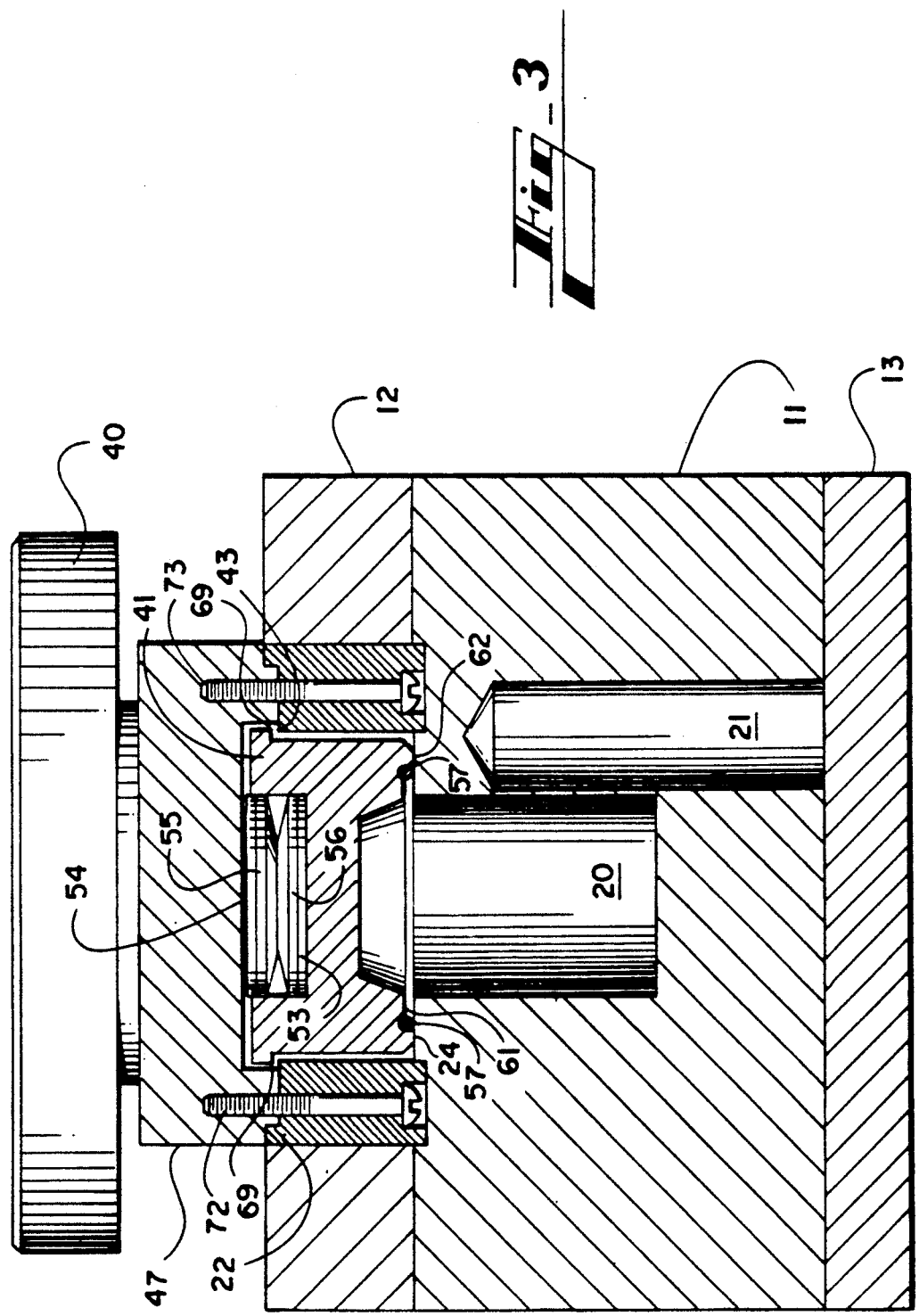

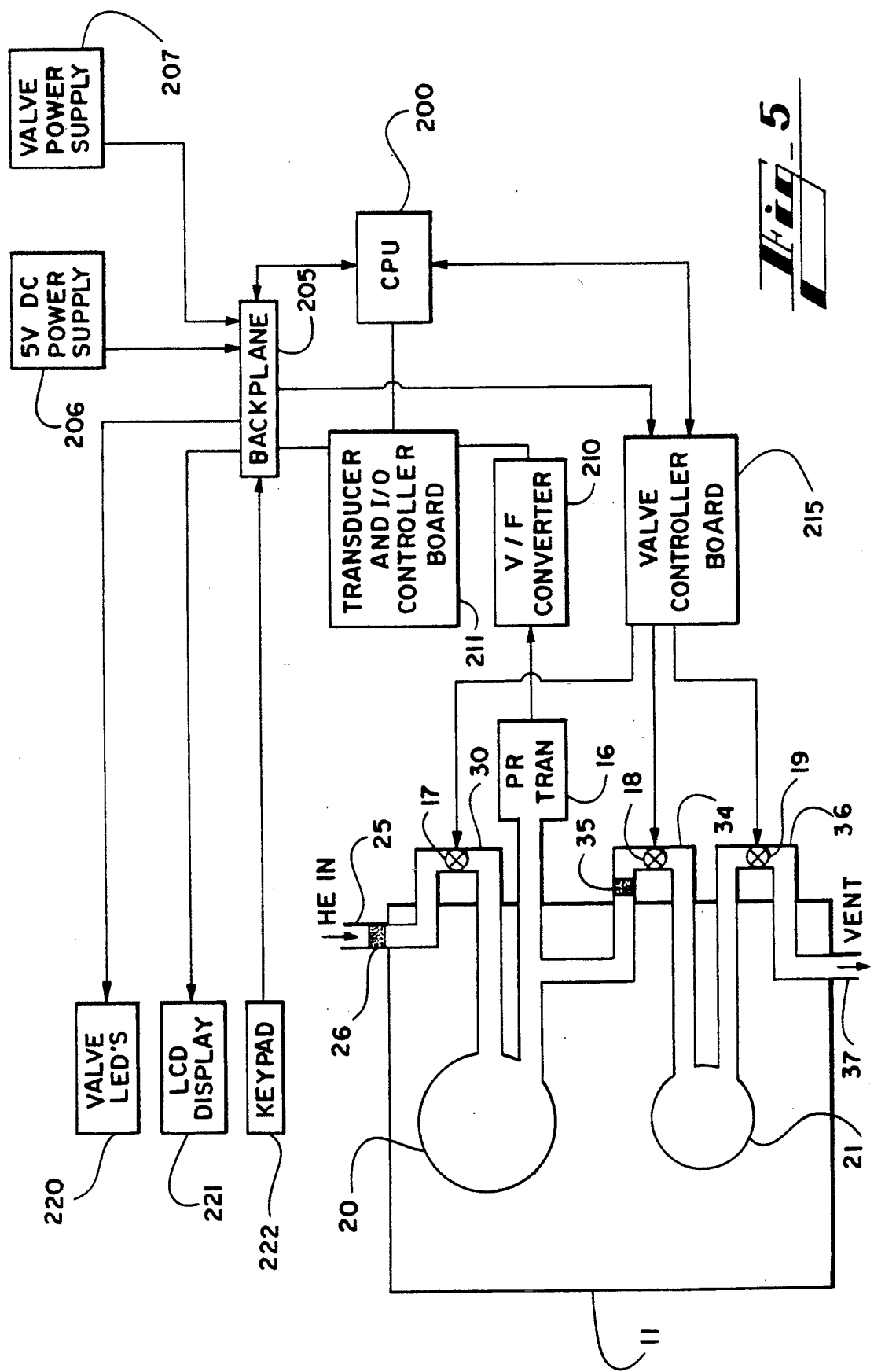

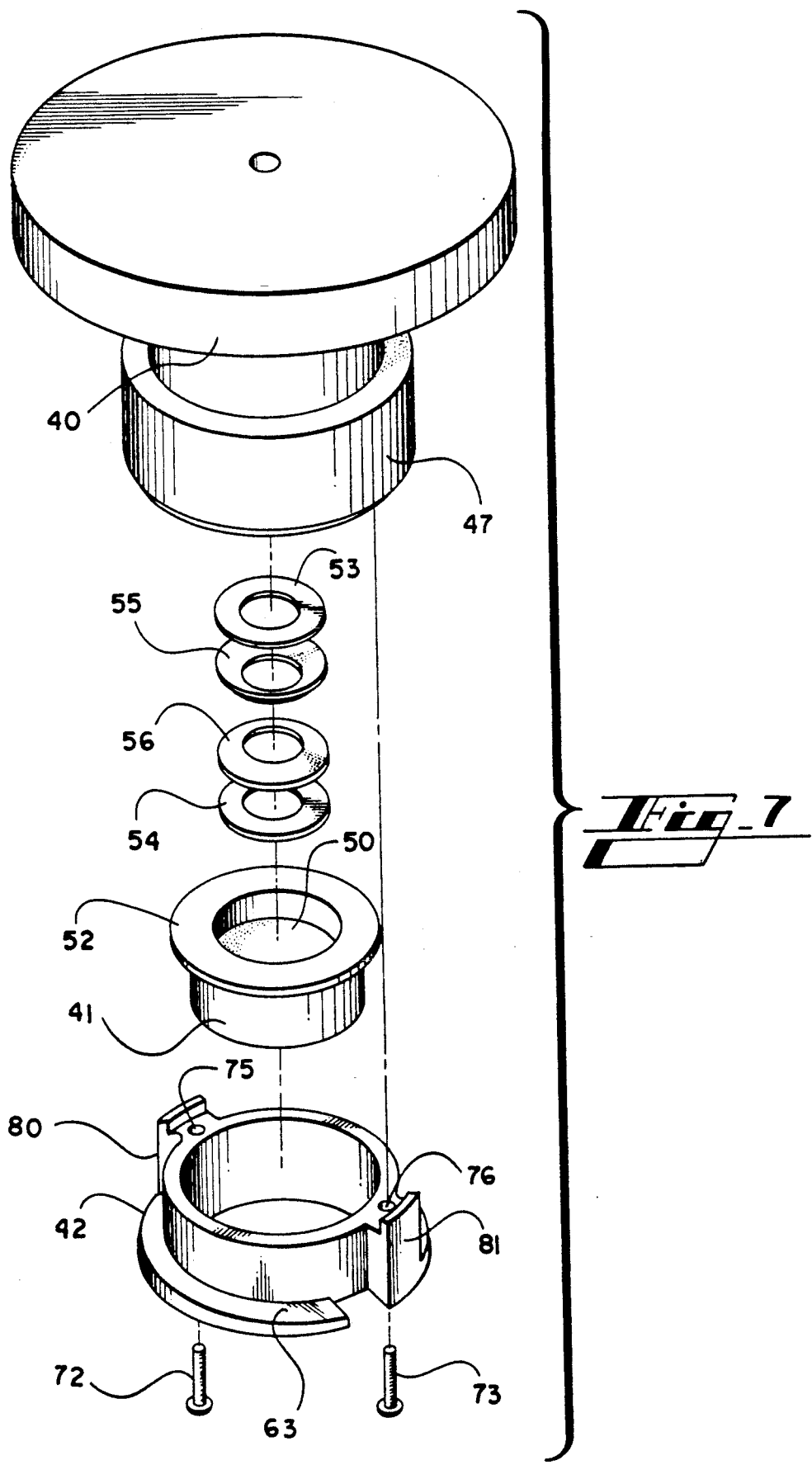

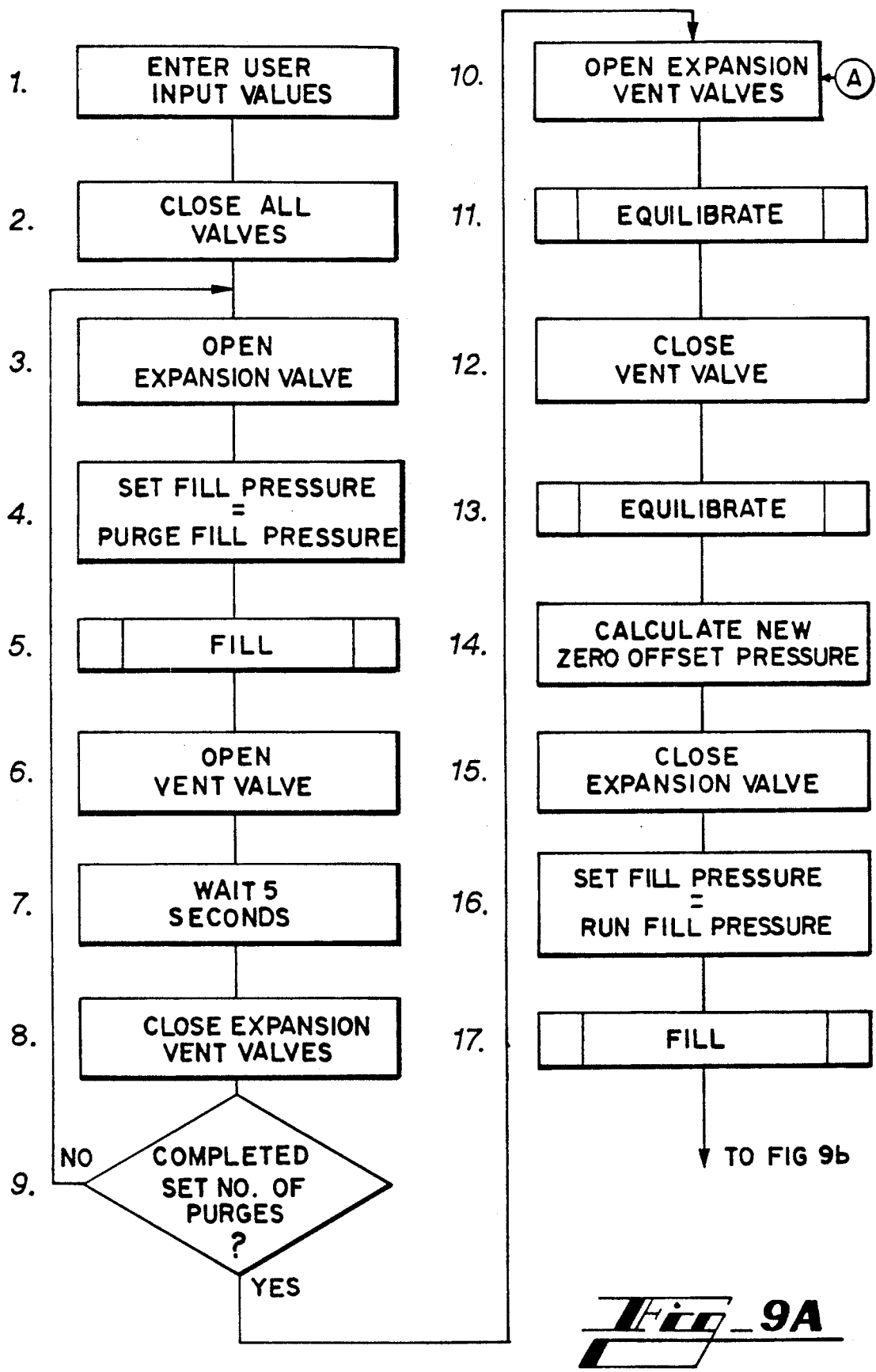
Fig_9A

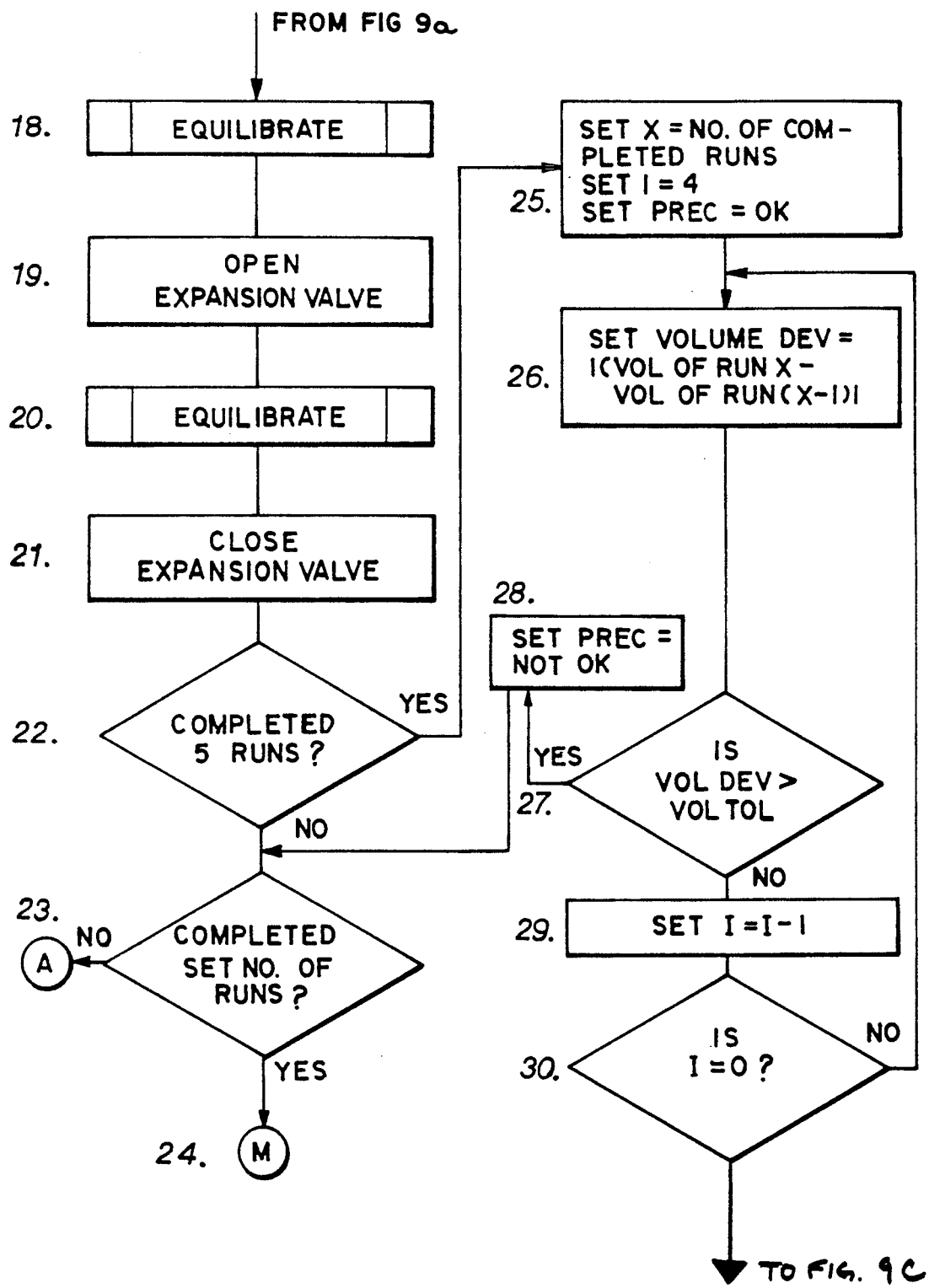
Fig_9B

GAS COMPARISON PYCNOMETER

FIELD OF THE INVENTION

The present invention relates to an apparatus for measuring the volume of a solid substance and more particularly to a pycnometer which has an automatic purging and run control system.

BACKGROUND OF THE INVENTION

The density of a substance, its mass divided by its volume, can be an identification parameter for pure substances, a composition descriptor for mixtures of two pure substances, an indicator of adulterations in preparations of otherwise known composition and a detector of voids in an apparently solid object.

Density must be accurately determined to provide the above information. The mass of a solid substance is easily and accurately determined with modern analytical balances, and volume is also easily and accurately established for solid substances of uniform geometric shape such as spheres and cubes. However, volume of irregularly-shaped solids such as minerals, commodities and many other substances of commercial significance, is not easily calculated.

Commercially available gas comparison pycnometers typically measure volumes of 50 cm$^3$ to a precision of ±0.1 cm$^3$. Greater precision is sorely needed if the measured density is to function as an identification parameter, a composition descriptor, an indicator of adulterations or a detector of voids. As is well known, such pycnometers operate by pressurizing gas around a sample in a chamber, measuring the pressure, allowing expansion of the gas into an additional chamber, and measuring the pressure in the combined volume. The result is compared to calibration data to determine the volume of the unknown sample.

Current gas comparison pycnometers suffer from many deficiencies which limit the precision of the volume determination. First, the devices are not stable against ambient temperature variations. Any change in room temperature can influence the pressure measured in either the sample chamber or the expansion chamber.

Second, when an expansion is made from the sample chamber into the expansion chamber, an internal gas energy change transpires. Its influence cannot be accounted for except by insuring that the pressure change encompasses identical limits.

Third, closure devices for the sample chamber do not adequately seal and reproducibly define the chamber to insure a constant volume when the test are run. An inadequate closure of the sample chamber greatly decreases the accuracy of the volume determination.

Fourth, problems arise when the sample is placed into the pycnometer. The sample may be at a temperature different from the pycnometer. Also, unwanted moisture and vapors enter the system when the sample is introduced into the pycnometer. The sample may itself contain large quantities of vapors which will cause the pressures to vary from the ideal values. These foreign vapors must be removed before a precise volume measurement can be achieved. Heretofore, unwanted moisture and vapors have been removed from the pycnometer by attempting to completely evacuate the system with a vacuum pump. Other devices remove the unwanted moisture and vapors by a prolonged flushing of the system with a steady, slow flow of helium. Other devices try to purge the system by manually alternatively increasing and decreasing the gas pressure in the sample chamber.

The above deficiencies can greatly affect the accuracy of the volume calculated by the pycnometer. However, no prior art pycnometers have a way to check the precision of its volume determination. Thus, there has been a need in the art for an apparatus exhibiting greater precision when determining the density of a solid substance.

SUMMARY OF THE INVENTION

The present invention solves the above problems in the art by providing a pycnometer which can quickly and accurately determine the volume and density of a solid substance.

Generally described, one aspect of the present invention provides an apparatus and method for determining and checking the accuracy of the volume of a substance. The sample to be tested is placed in a sample chamber with a fixed volume and a sequence of tests is carried out, monitored and compared until the results are within a set tolerance of being a constant value. Only then is this constant value accepted as the volume of the sample being tested. When it is determined that the volume reading is accurate, this volume is then used to calculate the density of the substance being tested.

In the preferred embodiment, a microprocessor controls performance of a sequence of test runs which provide the progression of results to the constant volume. The sample chamber is pressurized with a gas such as helium, and the pressure transducer measures the pressure in the sample chamber. The gas is then allowed to expand into the expansion chamber and the pressure is measured in the connected chambers. In the alternative, the expansion chamber may be pressurized with helium and the gas then allowed to expand into the sample chamber. The volume of the solid sample is calculated and stored. The sample and expansion chambers are then vented to atmosphere, and the above steps are repeated a predetermined number of times. The volume of the last run is compared to the volume of previous runs. If these volume comparisons or volume deviations are within a predetermined tolerance, uncontaminated helium has been established in the system and any temperature discrepancy between the sample and the system also has been dissipated. The volume of the last run is accepted as accurate and used for the density calculation. If the volume deviation is greater than the volume tolerance, test runs are repeated until the volume deviation over the final runs is less than the volume tolerance, or until an initially specified number of runs has been reached.

According to another aspect of the invention, the volume of the sample chamber remains fixed from run to run because of a unique closure device or cap assembly sealing the sample chamber. The cap assembly described above includes a rigid portion which engages the sample chamber to always define the same volume within the chamber. Mounted in the cap is a compressible gasket member. When the cap is inserted into the opening of the sample chamber, the gasket compresses against a continuous surface surrounding the opening of the sample chamber and insures a tight fitting sealing arrangement.

Another aspect of the present invention provides an improved method for purging the pycnometer system of unwanted moisture and vapors. This purging includes a particular routine for repeatedly pressurizing the sample chamber and the expansion chamber above atmosphere and then venting these chambers back to atmosphere. This method of purging provides a more efficient way to remove unwanted gas than prior continuous flow methods.

Thus, it is an object of the present invention to provide an apparatus which can accurately determine the volume of a solid substance.

It is a further object of the present invention to provide an apparatus which can accurately determine the density of a solid substance.

It is a further object of the present invention to provide an apparatus which can purge unwanted moisture and vapors quickly and efficiently from a pycnometer.

It is another object of the present invention to provide a pycnometer which can check the accuracy of its volume determination.

It is a further object of the present invention to provide a pycnometer apparatus with a closure device which can assure the same constant volume each time the closure device is engaged in a sealing arrangement.

Other objects and advantages of the present invention will become more readily apparent from the following description of a preferred embodiment.

BRIEF DESCRIPTION OF THE DRAWING

FIG. 1 is a pictorial view of the pycnometer apparatus embodying the present invention.

FIG. 2 is a vertical cross-sectional view taken along line 2—2 of FIG. 1.

FIG. 3 is a cross-sectional view taken along line 3—3 of FIG. 1.

FIG. 4 is a rear view of the apparatus of FIG. 1.

FIG. 5 is a schematic representation of the pneumatic and electrical circuits associated with the pycnometer shown in FIG. 1.

FIG. 7 is an exploded view of the elements of the cap assembly of FIG. 6.

FIGS. 9A, 9B, 9C are schematic flow diagrams of the overall operation of the pycnometer.

DETAILED DESCRIPTION OF PREFERRED EMBODIMENT

Figure 6:
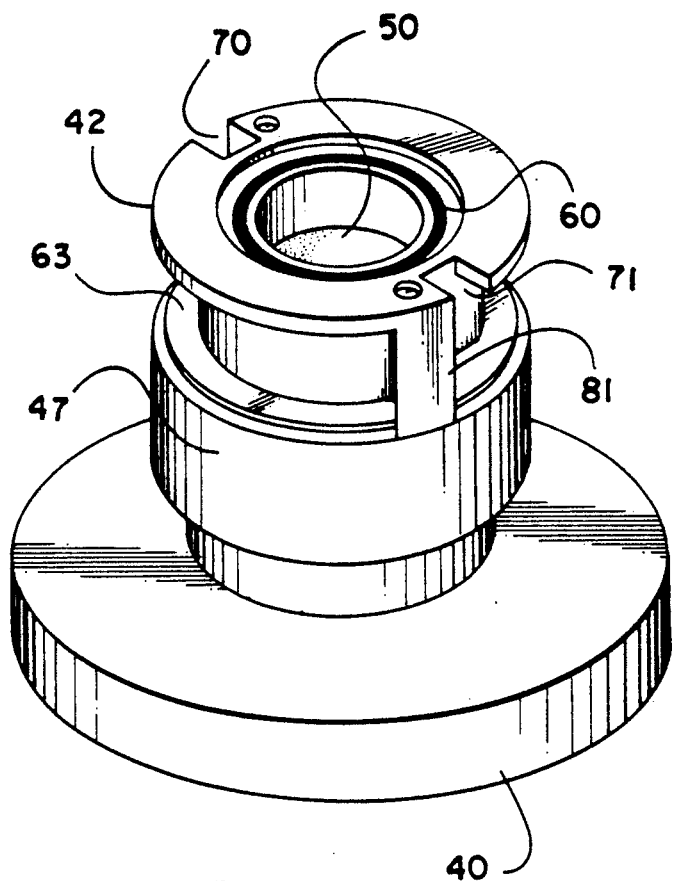
FIG. 6 is a pictorial view of the preferred embodiment of the cap assembly.

Referring now in more detail to the drawing in which like numerals refer to like parts throughout the several views, FIG. 1 shows a pycnometer 10 embodying the invention. Generally described, the pycnometer 10 includes a block 11, with a top plate 12 affixed to the top of the block. The block 11 rests on and is affixed to a bottom plate 13. The block 11, top plate 12, and bottom plate 13 are made of a material of high thermal conductivity such as aluminum. On the exterior of the pycnometer 10 are positioned a cap assembly 15, a pressure transducer 16 and valves 17, 18 and 19.

Referring to FIGS. 2, 3 and 5, the pycnometer 10 also includes a sample chamber 20, bored from above into the interior of the block 11. An expansion chamber 21 is also located in the interior of the block 11 and is formed by drilling upwardly from the bottom surface of the block. The volume of the expansion chamber 21 is approximately half the volume of the sample chamber. The two cavities are bored in close proximity to each other to ensure maximum temperature uniformity and stability.

A circular orifice 22 is located in the top plate 12, positioned over the opening of the sample chamber 20. This orifice 22 is sized to receive the cap assembly 15. The cap assembly 15, when placed through orifice 22 and twisted, seals the sample chamber 20 in a manner described below, thereby insuring a fixed volume in the chamber. Two rollers 65 are rotatably mounted on shafts 66 projecting inwardly horizontally from opposite sides of the wall of the orifice 22. As described below, the cap assembly 15 engages the rollers 65 when the chamber is being sealed.

Located on the top surface of the block 11 and surrounding the opening of the sample chamber 20 is a horizontal annular platform 24. The platform 24 is within the circumference of the orifice 22, and provides a smooth bearing surface for parts of the cap assembly 15. Surrounding the annular platform 24 is an annular groove 25. The circumference of the annular groove 25 is equal to the circumference of the circular orifice 22 and the circumference of a ramp 42 (described in detail below) of the cap assembly 15. The groove 25 matingly receives the ramp 42 when the cap assembly 15 is sealing the sample chamber 20.

An inlet line 25 extends from a source of gas (not shown) through the top plate 12 and connects to a first valve 17 positioned on the exterior of block 11. The inlet line 25 allows the introduction of a gas such as helium into the pycnometer 10. A first flow restrictor 26 is placed on the inlet line 25 before it enters the interior of the block 11. The first flow restrictor 26 is a highly compacted and small metal filter or a length of small inner diameter tubing and its function is to control the inlet gas rate and the rise of gas pressure in the sample chamber 20.

Extending from the first valve 17 is a passageway 30 drilled horizontally into the interior of the block 11. This passageway 30 connects the first valve 17 with the sample chamber 20. A second passageway 31, also drilled horizontally into the interior of the block 11, extends from the bottom of the sample chamber 20 to a pressure transducer 16 located on the exterior of the block. The pressure transducer 16 measures the gas pressure in the sample chamber 20.

Another passageway 34 joins the sample chamber 20 with the expansion chamber 21. A second flow restrictor 35 and valve 18 are located in this passageway. This second flow restrictor 35, placed upstream from the valve 18, limits the rate of pressure decrease in the sample chamber 20 thereby avoiding fluidization and carryover of particles from the sample chamber 20 into the expansion chamber 21. The valve 18 controls the gas flow between the sample chamber 20 and expansion chamber 21.

A fourth passageway 36 is drilled horizontally into the block 11 and connects the expansion chamber 21 to an exhaust line 37. A third valve 19 is located within the passageway 36 and controls the venting of gas out of the expansion chamber 21 into the environment. The exhaust line 37, the valves 17, 18, 19 and the pressure transducer 16 are all positioned on the rear wall of the pycnometer block 11.

The cap assembly 15 is illustrated in FIGS. 6 and 7. A knob 40 is found on the top portion of the cap assembly 15. A series of projections surround the top periphery of the knob 40, enabling the operator to securely grip and twist the cap assembly 15 into its proper sealing position. The know is attached to a sealing cup housing 47 which defines a cylindrical recess 46 in its lower surface.

Figure 8:
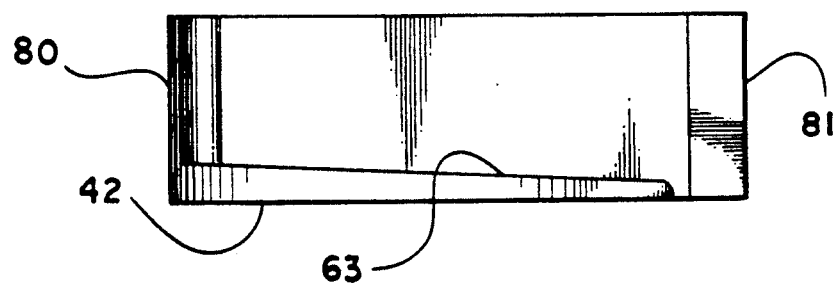
FIG. 8 is a side plan view of the ramp shown in FIG. 9.

Attached to the lower surface of the housing 47 is an annular ramp 42, as shown in FIGS. 6, 7 and 8. Inclines 63 and 64 are defined on either side of the ramp 42. Removal of material to form inclines 63 and 64 creates an L-shaped cross-section in two sections of the ramp 42, with the inclines forming the horizontal leg of the "L" at the bottom of the ramp. The vertical leg forms an inner wall 43 of the ramp 42.

The two inclines 63 and 64 are separated by solid sections 80, 81 through which screw openings 75, 76 are formed on the bottom of the ramp 42. Cutouts 70, 71 are formed in the inclines adjacent the solid sections 80, 81.

The cap assembly 15 includes a generally cylindrical sealing cup 41 positioned within the recess 46 of the housing 47 and the center of the ramp 42. The sealing cup 41 is preferably formed from aluminum. A circular recess 50 is formed in the top surface of the sealing cup 41. This recess 50 is sized to hold two flat washers 53 and 54 and two belville washers 55 and 56. The sealing cup 41 also includes a recess 51 formed in its bottom surface.

An annular groove 57 surrounds the opening of the recess 51. A lightly greased O-ring 60 is placed into the interior of the groove 57.

An inner annular surface 61 is located between the opening of the frustoconical recess 51 and the annular groove 57. An outer annular surface 62 is located between the groove 57 and the exterior cylindrical surface of the sealing cup 41. The outer annular surface 62 makes metal-to-metal contact with the horizontal annular platform 24 surrounding the opening of the sample chamber 20 when the chamber is sealed. The inner annular surface 61 does not make metal-to-metal contact when the cap assembly 15 is sealing the sample chamber 20, but rather defines a gap which is a part of the fixed volume of the sample chamber.

At the upper surface of the sealing cup 41, an annular flange 69 surrounds the cup 41, extending beyond the vertical wall 43 of the ramp 42, but ending within the walls of the cylindrical recess 46 of the housing 47. Thus, the sealing cup 41 can move vertically with respect to the housing 47 and the ramp 42, through a short distance, but is entrapped by the wall 43 and cannot fall out of the cap assembly 15. Furthermore, the washers 55 and 56 are sized to urge the cup 41 outwardly from the housing 47.

Assembly of the cap assembly 15 is illustrated in FIG. 7. Two screws 72, 73 are threaded through the screw openings 75, 76 and attach the ramp 42 to the housing 47, confining the sealing cup 41 as described above.

After the sample to be analyzed is placed in the sample chamber 20, the operator places the cap assembly 15 into the orifice 22. The operator must align the cap assembly 15 such that the cutouts 70, 71 will permit the rollers 65, 66 to pass through the bottom of the ramp 42, thereby engaging the inclines 63, 64. The cap assembly 15 is now ready to seal the sample chamber 20.

To effect this sealing operation, the operator twists the cap assembly 15 in a counter-clockwise direction, moving the inclines 63, 64 along the rollers 65, 66 which apply a downward force on the cap assembly. The belville washers 55, 56 then urge the sealing cup 41 onto the platform 24. This camming actions ensures metal-to-metal contact between the surface 62 of the sealing cup 41 and the platform 24, as well as the compression of the O-ring 60 against the platform 24. The volume of the sample chamber 20 is now fixed, and the pycnometer 10 is ready for operation.

The cap assembly 15 shown in FIG. 6 is rotated counter-clockwise to generate a sealing force, and therefore is left-handed. It will be appreciated that the cap can also be designed to be right-handed.

FIG. 5 illustrates how the pycnometer 10 is used in conjunction with a conventional microprocessor. The microprocessor controls the various elements of the system during operation in a manner described below. In a conventional manner, the computer operates valves 17, 18 and 19 as well as monitoring the pressure measurements taken by the pressure transducer 16. The computer also accepts the various keypad inputs and provides the appropriate displays, such as LED's and LCD's.

The central processing unit 200 plugs into a backplane 205. The backplane 205 is the main communication bus interconnecting the entire system. A power supply board 206 also plugs into the backplane 205 and is a regulated 5 V DC for digital logic. This power supply board 206 supplies power to everything in the system except for valves 17, 18 and 19.

The valves 17, 18 and 19 are powered by a valve power supply 207, which also plugs into the backplane 205. The valves take a maximum of 15 instantaneous watts to drive and require a 20 V pulse, 35 msec in duration, to open or close. It is important that the valves 17, 18 and 19 do not generate excess heat when opening and closing due to the possibility of changing the temperature of the block 11 and affecting test results. Therefore, the valves are operated with a pulse of current rather than having a continuous current supply.

A voltage to frequency (V to F) converter 210 receives the output of the pressure transducer 16 and is connected to a transducer and input/output (I/O) controller board 211. The I/O controller board 211 is also plugged into the backplane 205. The V to F converter 210 takes the voltage output from the pressure transducer 16 and converts it to a pulse train whose frequency is proportional to the voltage output from the pressure transducer. The output of the board 211 is directed to the CPU 200 through the backplane 205. A basic analog to digital conversion is performed wherein these pulses are integrated over a fixed period of time, arriving at a number that is proportional to the output of the pressure transducer 16.

A valve controller board 215 contains all the logic for controlling the valves, 17, 18 and 19 in response to signals from the CPU. This valve controller board 215 is connected to the CPU 200 and also to the backplane 205.

Completing the electronics of this system are conventional valve LED's 220, an LCD display 221 and keypad 222, all three plugged directly into the backplane 205. The I/O controller board 211 also contains logic for handling user input through the keypad 222, and output to the set of LED's 220, which display the open or closed status of the valves, and the LCD display 221, which displays run status messages, error messages, and results of the analysis. Output to compatible devices through an RS-232 connector or similar interface (not shown) can also be provided.

The above-described electronic components are conventional. However, automatic operation and control readily permits the helium to be established about the sample. Computerization of the pycnometer 10 allows pressure measurements to be carried out rapidly so that external influences such as ambient temperature and pressure changes have no time to exert significant effects on test results. Also rapid repetitive testing allows attainment of a constant value reading thereby signaling a uniform temperature throughout the pycnometer 10 and insuring accurate test results.

Operation of the pycnometer 10 is described as follows, with particular reference to the flow charts of FIGS. 9, 10 and 11 which shown a sequence of steps taken by the operator and performed by the pycnometer.

Figure 9C:
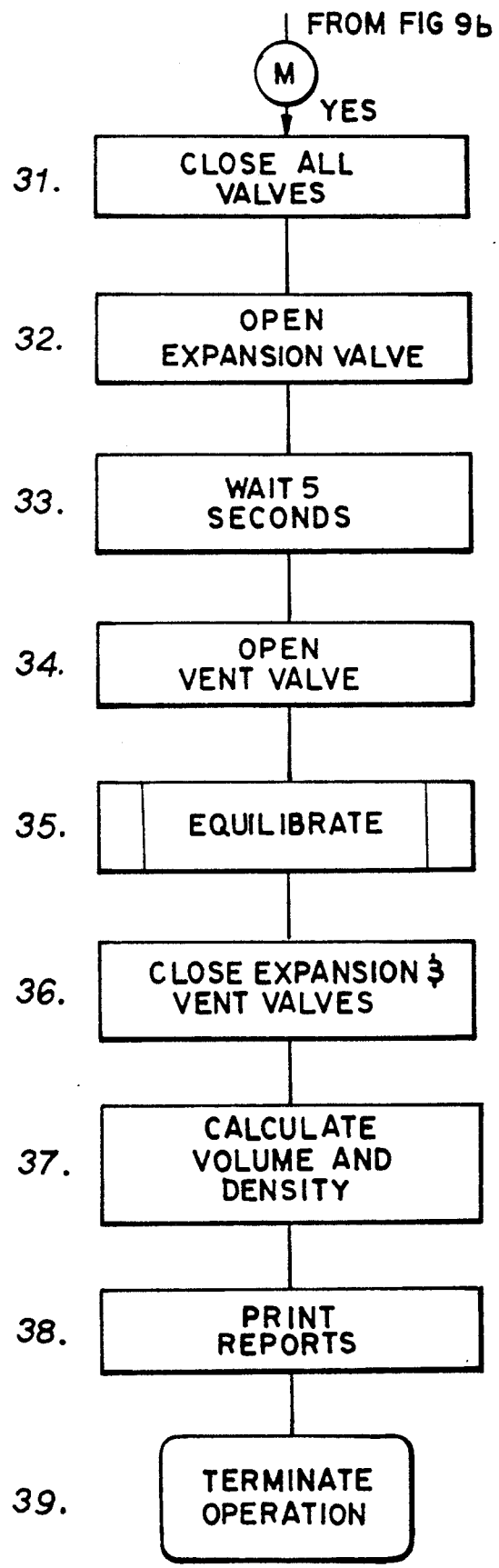
Figure 10:
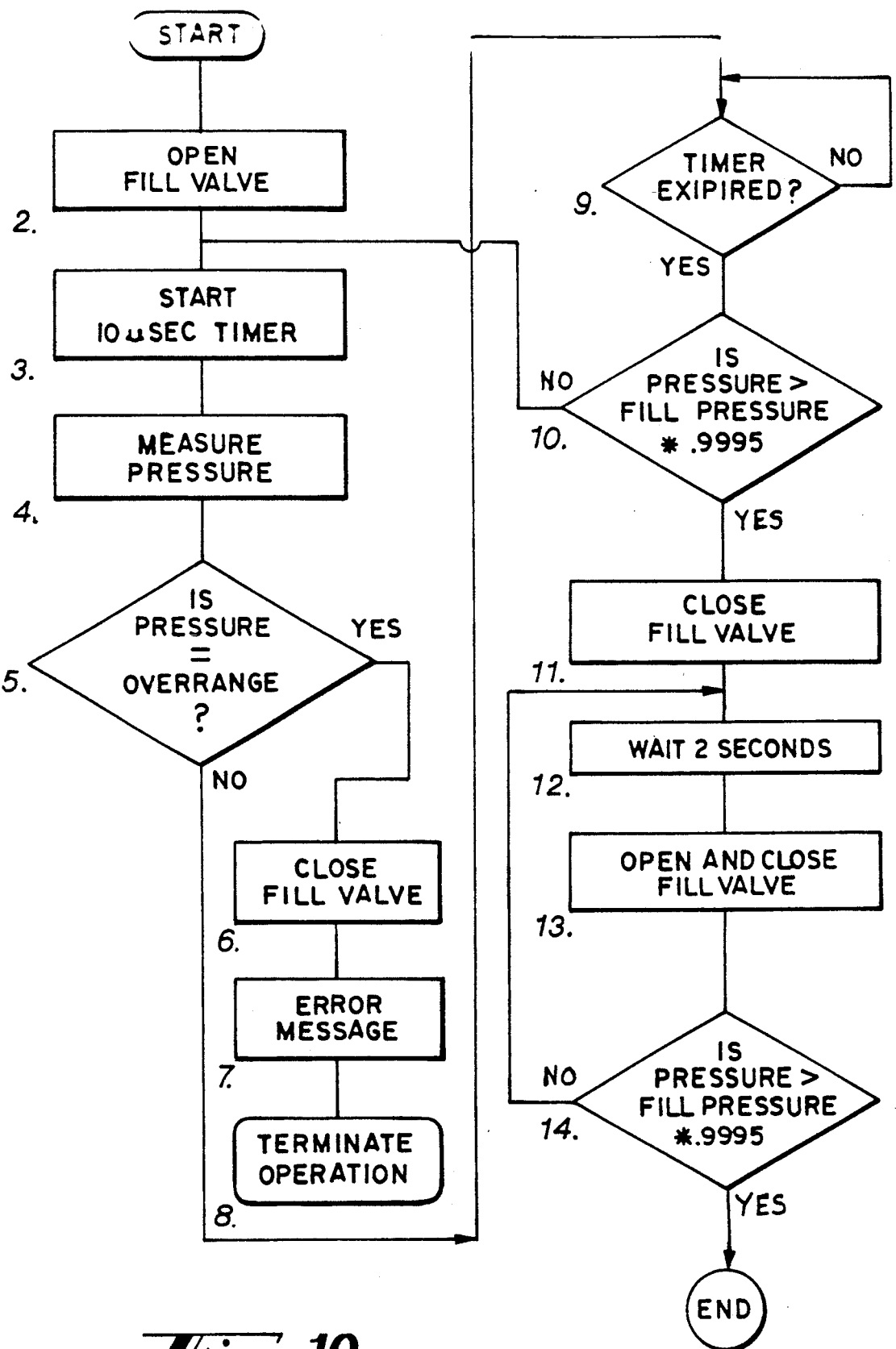
FIG. 10 is a schematic flow diagram of the fill sequence utilized in the operation of the present invention.

Describing the operation of the system in more detail, block 1 of FIG. 9 indicates the parameters and instructions the operator must input in order for the system to carry out an analysis. These values include the number of purges, the purge fill pressure, the run fill pressure, the maximum number of run attempts, the acceptable equilibrium rate, and the volume tolerance defining an acceptable result. These values and their significance will be explained in detail below. After these values are input by the operator, valves 17, 18 and 19 are closed.

Before operating the apparatus to determine the volume of a sample, the pycnometer 10 must be flushed or purged of all unwanted moisture and other condensable vapors that entered when the sample was manually deposited inside the sample chamber 20.

This purging ensures the accurate calculation of the volume of the sample. The purging infuses the chambers and passageways with helium. The sample chamber 20 and expansion chamber 21 are pressurized above atmospheric pressure and then expanded back to atmospheric pressure. This step of pressurizing above atmosphere and then expanding back to atmosphere is repeated for a set number of purges. These series of purges will desorb and expel the unwanted vapors and gases from the chamber and passageways.

Blocks 3-9 of FIG. 9 illustrate the purging action performed by the pycnometer to flush the unwanted gases. The expansion valve 18 is open and the fill pressure is set to purge fill pressure. In block 5, helium is then introduced into the sample chamber 20 according to the "fill" routine of FIG. 10. In block 2 of FIG. 10, valve 17 is opened and a 10 millisecond timer is activated. The pressure transducer 16 measures the pressure inside the sample chamber 20. The pycnometer 10 is then tested to make sure the gas injectors are mechanically functioning properly and not overpressurizing the system. If the gas injectors do not meet the required purge fill pressure within 300 seconds, or if the system is overfilled, the fill valve 17 will close and the operation is terminated because of an error situation. If the system is not overpressurized, the pressure is measured in the sample chamber 20 after a period of 10 milliseconds has elapsed from the time after the fill valve 17 was opened, as determined in block 9. This pressure measurement is then tested to see if it is at least 99.95% of the purge fill pressure. If it is not within this tolerance, the 10 millisecond timer is activated again and the sequence in blocks 3-10 is repeated until the pressure measurement is within the predetermined tolerance of 99.95% of the purge fill pressure.

Once the pressure measurement is within this predetermined tolerance, the fill valve 17 is closed. The instrument waits two seconds and checks the pressure. If it is below the required tolerance, the fill valve 17 is briefly opened and then shut. The instrument repeats this series of steps until the pressure has stabilized to at least 99.95% of the fill pressure. The program returns to block 6 of FIG. 9, and the vent valve 19 opens, allowing the unwanted gases to be flushed out of the system. The sequence for purging the system in blocks 3-8 of FIG. 9 is repeated until the set number of purges, inputted by the operator, is reached in block 9. In the preferred embodiment, the number of purges needed to adequately flush the pycnometer 10 of moisture and other condensable vapors is variable from three for dry, nonporous samples up to 99 which might be required for moist, porous samples of high affirmity for water vapor or other gases. More frequently, the usual sample will require five to ten purges.

After the purging of the pycnometer 10 of unwanted vapors is complete, the computer will then execute a zeroing operation to establish a base line atmospheric pressure in the pycnometer 10. In block 10 of FIG. 9, the expansion valve 18 and vent valve 19 are opened. Equilibrium in the system is established in block 11, according to the "equilibrium" routine of FIG. 11. In block 1 of FIG. 11, a high precision pressure reading is selected by the system. The pressure in the sample chamber 20 is measured by the pressure transducer 16 approximately once each second. If the pressure reading is equal to an overrange pressure, the operation is terminated. If the pressure is not overrange and eight seconds has elapsed, the equilibrium pressure is calculated by using a conventional Savitsky-Golay nine point smoothing routine to fit a curve with four prior and four subsequent pressure readings. A Savitsky-Golay eleven point smoothing routine could also be used.

The equilibrium rate, or how fast the pressure is changing within the sample chamber 20, is then determined. The equilibrium rate is calculated using a conventional nine point differential smoothing routine. This curve is fit with four prior and four subsequent smoothed equilibrium pressures calculated in block 7 of FIG. 11.

Figure 11:
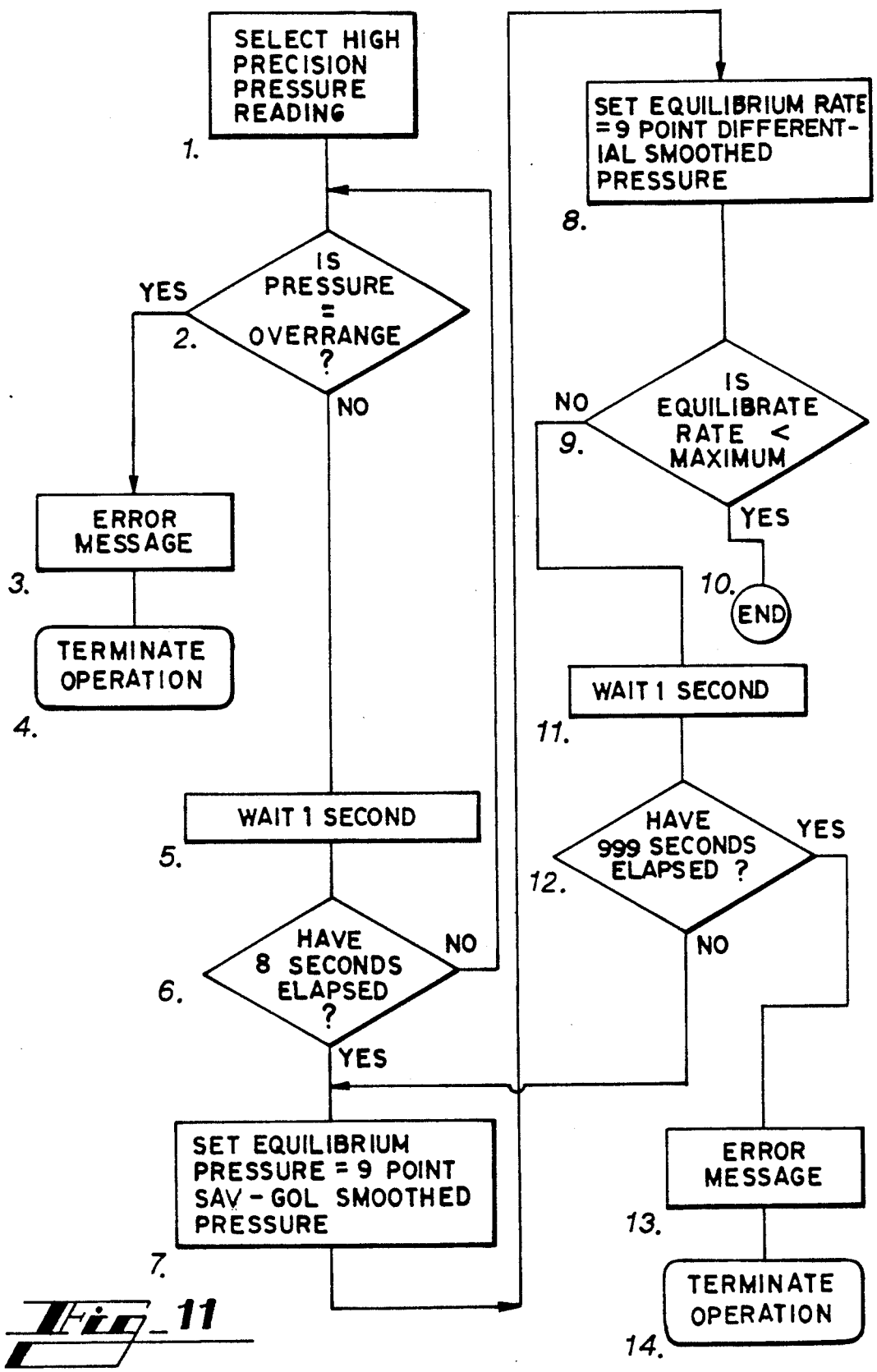
FIG. 11 is a schematic flow diagram of the equilibration sequence utilized in the operation of the present invention.

After the equilibrium rate is calculated in block 8 of FIG. 11, it must be compared to the previously set maximum allowable rate of pressure change. If the equilibrium rate is less than or equal to the maximum, the equilibration subroutine is completed. If, however, the equilibrium rate is greater than the maximum, the operating sequence in blocks 7-9 is repeated until the system is equilibrated, or a maximum time period has expired, as tested in block 12. If the system cannot equilibrate within the maximum time allowed, an error message is produced in block 13 and operation is terminated.

Referring to block 12 of FIG. 9, the vent valve 17 is closed and the equilibrium subroutine illustrated in FIG. 11 and described hereinabove is repeated. After the second equilibration sequence, a new zero offset pressure is calculated. This pressure establishes a baseline atmospheric pressure in the system before tests on samples are run. The expansion valve 18 is closed and the system is now ready to analyze the unknown sample previously deposited into the sample chamber 20.

Blocks 16-39, FIG. 9, refer to the run routine executed by the computer. In block 16 of FIG. 9, the fill pressure is set to the run fill pressure. The sequence for filling the system in FIG. 10 is then repeated to fill the sample chamber 20 to the run fill pressure. After the filling subroutine is complete, the computer then executes the equilibration subroutine illustrated in FIG. 11. After the system is equilibrated, the expansion valve 18 is opened and the helium expands into the expansion chamber 21. The system is then equilibrated, since to insure optimum test results, equilibrium pressures must be carefully established both before and after each expansion.

Referring now to block 21 of FIG. 9, the expansion valve 18 is closed after equilibrium. The zeroing and run sequences in blocks 10-21 of FIG. 9, are repeated until five runs have been completed as tested in block 22. When five runs have been completed according to the preprogrammed schedule, a sequence of tests are performed comparing the five runs, to make evident the presence or absence of a progression of results to a constant value. The constant value happens to be the sample volume. Its attainment signals that uncontaminated helium has been established and any temperature discrepancy between the sample and the system has been dissipated.

Blocks 25-30 of FIG. 9 illustrate the above-described sequence of tests. These sequence of tests are in essence a volume check test to determine if the volume deviation between the five successive runs is within the previously set volume tolerance. After five runs are completed, the volume of the first run is subtracted from the volume of the fifth, or last run. The absolute value of this number is termed the volume deviation. If the volume deviation is less than the allowable volume tolerance, the sequence in blocks 25-30 is repeated calculating the volume deviation between the fifth or most recent run and the second, third and fourth run, respectively, in that order.

If the volume deviation between the fifth and four previous runs is within the predetermined volume tolerance, the system concludes that the constant value referred to above is reached and a Boolean variable representing adequate precision is taken to be true. At this point, valves 17, 18 and 19 are closed, in block 31 of FIG. 9. The expansion valve 18 is then opened; after five seconds the vent valve 19 is opened and the system is allowed to equilibrate to atmospheric pressure. After the equilibration is complete, the expansion valve 18 and vent valve 19 are closed. Volume and density are calculated in block 37, output reports are printed and operation is terminated.

If, however, the volume deviation as tested in block 27 is greater than the volume tolerance during any one of the sequence tests in blocks 25-30 of FIG. 9, the precision is set as not correct in block 28 and the pycnometer will repeat the zeroing and run operations described in blocks 10-22. After this additional run, the computer will determine the volume deviation between the most recent run and the four runs preceding it. Only if the volume deviation is less than the volume tolerance in five successive runs, will a constant value be accepted. If this constant value is not attained after a maximum set number of runs, tested in block 23, the operation is terminated.

The detailed description of the operation of the pycnometer in conjunction with a computer has been described hereinabove and illustrated in the flow charts of FIGS. 9, 10 and 11. The following discussion merely describes the theory behind determining the volume of a sample placed inside the pycnometer, used in performing the calculations of block 37 of FIG. 9. The discussion does not reflect the entirety of operations performed by the computer when ascertaining the volume of the sample.

The pycnometer 10 is of the comparison design. Therefore, it first must be calibrated. Two tests must be performed since the two volumes of the sample chamber 20 and the expansion chamber 21 must be established. The first test is run pursuant to the flow charts described above without any sample in the sample chamber 20. Both chambers should contain gas at ambient pressure or zero gauge pressure and valves 17, 18 and 19 should be closed. Valve 17 is opened and the sample chamber 20 is charged to $P_1$ gauge pressure by introducing helium into the sample chamber by way of the inlet line 25 and passageway 30. Pressure transducer 16 reads $P_1$.

The computer then closes valve 17 and opens valve 18. The helium then travels through passageway 34 expanding into the expansion chamber 21, thus reducing the pressure in the sample chamber 20 to $P_2$. This pressure is read and recorded by the pressure transducer 16. Valve 19 is opened, allowing the helium to exit the pycnometer 10 by way of passageway 36. The following relationship is obtained:

$$P_1 V_C = P_2(V_C + V_E). \quad (1)$$

where
$P_1 = P_1$ gauge pressure in sealed sample chamber;
$V_C =$ volume of sample chamber;
$P_2 = P_2$ gauge pressure taken after expansion into expansion chamber; and
$V_E =$ volume of expansion chamber.

Next, an object of known volume $V_K$ is placed in the sample chamber 20 and the operator repeats the above steps of introducing the helium into the sample chamber and allowing it to expand into the expansion chamber. The following relationship is obtained:

$$P_1^*(V_C - V_K) = P_2^*(V_C - V_K + V_E). \quad (2)$$

Where:
$V_k =$ volume of known sample;
$V_C =$ volume of sample chamber;
$V_E =$ volume of expansion;
$P_1^* =$ before expansion pressure with known volume; and
$P_2^* =$ after expansion pressure with known volume.

Solving equation (1) for $V_E$ gives:

$$V_E = V_C[(P_1 - P_2)/P_2] \quad (3)$$

Equation 3 establishes the relationship between $V_E V_C$. Incorporating equation 3 into equation 2 and solving for $V_C$ yields the following equation:

$$V_C = V_K(P_1^* - P_2^*)/[(P_1^* - P_2^*) - (P_1 - P_2)(P_2^*/P_2)] \quad (4)$$

Equations (3) and (4) establish the respective volumes of the sample chamber and expansion chamber. The volume of the unknown sample is now determined.

The same above described steps are performed by the system to determine the volume of the unknown sample. First, this sample is placed in the sample chamber 20 and the operator properly pushes and twists the cap assembly 15 into the block 11. The sample chamber 20 should be sealed and its volume fixed. As performed during the calibration stage and described in detail above, helium is introduced into the pycnometer 10, and the pressure transducer 16 reads the $P_1^*$ pressure. The gas is then expanded into the expansion chamber 21 and $P_2^*$ is read by the pressure transducer 16. The following equation is obtained:

$$P_1^*(V_C - V_U) = P_2^*(V_C - V_U + V_E) \tag{5}$$

Solving for the volume of the sample $V_U$ gives $$V_U = V_C - [V_E/(1 - P_1/P_2)] \tag{6}$$

Hence, using equation 6, the volume of the unknown can be ascertained because $V_C$ and $V_E$ were determined from equations 3 and 4 respectively and $P_1^*$ and $P_2^*$ were recorded by the pressure transducer.

It should be understood that the foregoing relates only to a preferred embodiment of the present invention, and that numerous changes and modifications therein may be made without departing from the spirit and scope of the invention as defined in the following claims.

What is claimed:

1. An apparatus for determining the volume of a solid substance comprising:
   a sample chamber containing said substance;
   an integral expansion chamber connected by a passageway to said sample chamber;
   gas supply means for introducing a gas under pressure into one of said chambers;
   valve means for controlling flow of gas through said passageway;
   vent means for venting either of said chambers to atmosphere;
   means for measuring the pressure of gas within said one of said chambers; and
   control means for:
   (a) operating said gas supply means to pressurize with a gas the one of said chambers containing said pressure measuring means;
   (b) operating said pressure measuring means to measure the pressure in said one chamber;
   (c) operating said valve means to allow expansion of said gas through said passageway into said other chamber;
   (d) operating said pressure measuring means to measure the pressure in said connected chambers;
   (e) calculating a first volume of said sample;
   (f) storing said first volume;
   (g) operating said vent means to vent said chambers to atmosphere;
   (h) repeating (a) through (d);
   (i) calculating an additional volume of said sample;
   (j) comparing two or more of said volumes;
   (k) responsive to said compared volumes being within a predetermined tolerance, accepting one of said compared volumes as the volume of said sample; and
   (l) responsive to said compared volumes being outside said predetermined tolerance, repeating steps (h)–(j) until said compared volumes are within said predetermined tolerance.

2. A method for determining the volume of a solid substance contained in a sample chamber of a pycnometer having an integral expansion chamber and a passageway connecting said chambers comprising the steps of:
   (a) pressurizing one of said chambers with a gas;
   (b) measuring the pressure in said pressurized chamber;
   (c) allowing expansion of said gas into said other chamber;
   (d) measuring the pressure in said connected chambers;
   (e) calculating a first volume;
   (f) storing said first volume;
   (g) venting said chambers to atmosphere;
   (h) repeating steps (a) through (d);
   (i) calculating an additional volume of said sample;
   (j) comparing two or more of said volumes;
   (k) accepting one of said compared volumes as the volume of said sample if said compared volumes are within a predetermined tolerance; and
   (l) repeating steps (h) through (j) if said compared volumes are outside said predetermined tolerance until said compared volumes are within said tolerance.

3. A pycnometer apparatus comprising:
   a sample chamber containing a substance;
   an integral expansion chamber connected by a passageway to said sample chamber;
   gas supply means for introducing a gas under pressure into one of said chambers through a gas supply valve;
   expansion valve means for controlling flow of gas through said passageway;
   vent valve means for venting either of said chambers to atmosphere;
   means for measuring the pressure of gas within said one of said chambers; and
   control means for:
   (a) operating said supply valve so as to admit gas into said one chamber until the pressure within said one chamber approaches a predetermined fill pressure in said one chamber within a predetermined tolerance of said fill pressure;
   (b) closing said supply valve;
   (c) operating said pressure measuring means;
   (d) generating an error signal if the pressure in said one chamber exceeds said fill pressure by more than said tolerance;
   (e) momentarily admitting additional gas if the pressure in said one chamber is lower than said fill pressure by more than said tolerance;
   (f) repeating functions (b) through (e) until the pressure in said one chamber is within said tolerance; and
   (g) operating said expansion valve means to allow expansion of said gas through said passageway into said other chamber.

4. The apparatus of claim 3, wherein said supply valve, said vent valve means and said expansion valve means each comprises a pulse operated valve.

5. The apparatus of claim 4, wherein said chambers, said valves, and said pressure measuring means are contained within a single block of material of high thermal conductivity.

6. The apparatus of claim 5, wherein said material of high thermal conductivity comprises aluminum.

7. The apparatus of claim 4, further comprising:
   first restrictor means for limiting the flow rate of gas between said gas supply means and said one chamber; and
   second restrictor means for limiting the flow rate of gas between said chambers.

8. A method for determining the volume of a substance contained in a sample chamber of a pycnometer having an integral expansion chamber and a passageway connecting said chambers comprising the steps of:
- (a) pressurizing one of said chambers with a gas to establish a predetermined fill pressure in said one chamber within a predetermined tolerance of said fill pressure;
- (b) admitting said gas until the pressure in said one chamber approaches said predetermined fill pressure;
- (c) measuring the pressure in said one chamber;
- (d) generating an error signal if the pressure in said one chamber exceeds said fill pressure by more than said tolerance;
- (e) momentarily admitting additional gas if the pressure in said one chamber is lower than said fill pressure by more than said tolerance;
- (f) repeating steps (b) through (e) until the pressure in said one chamber is within said tolerance;
- (g) allowing expansion of said gas into said other chamber;
- (h) measuring the pressure in said connected chambers;
- (i) calculating the volume of said substance.

9. The apparatus of claim 1 further comprising a removable closure device to be placed in an opening defined by said sample chamber.

10. The apparatus of claim 9, wherein said removable closure device comprises:
- an annular surface surrounding said opening defined by said chamber;
- a cap including a mating surface, said mating surface engaging said annular surface to define said fixed volume when said cap is in a sealing position with respect to said opening;
- a compressible gasket member mounted in said cap such that said gasket member is compressed in sealing relationship against said annular surface when said cap is in said sealing position; and
- means for selectively retaining said cap in said sealing position.

11. The apparatus of claim 9, wherein said removable closure device comprises:
- a continuous surface surrounding said opening defined by said chamber;
- a cap including a rigid portion engaging said chamber to define said fixed volume when said cap is in a sealing position with respect to said opening;
- a compressible gasket member mounted in said cap such that said gasket member is compressed in sealing relationship against said continuous surface when said cap is in said sealing position; and
- means for selectively retaining said cap in said sealing position.

12. The apparatus of claim 11 wherein said cap comprises:
- a body;
- a plunger mounted for movement with respect to said body, said plunger defining said rigid portion and carrying said gasket member; and
- means for urging said plunger away from said body such that when said cap is in said sealing position, said plunger engages said continuous surface and said gasket is compressed.

13. The apparatus of claim 12, wherein said rigid portion defined by said plunger comprises an annular projection shaped to be matingly received by said continuous surface; and said gasket member comprises an O-ring received in a groove defined in said annular projection.

14. The apparatus of claim 12, wherein said means for selectively retaining said cap in said sealing position engages said body while permitting movement of said plunger.

15. The apparatus of claim 14, wherein said chamber is defined within a housing; and wherein said means for selectively retaining said cap in said sealing position comprises screw fastener means for joining said body and said housing.

16. The apparatus of claim 12, wherein said means for urging said plunger comprises a spring interposed between said body and said plunger.

17. The apparatus of claim 12, wherein said plunger is slidably mounted for movement within a cavity defined in said body.

18. The apparatus of claim 17, wherein means for urging said plunger comprises a spring mounted in said cavity between said body and said plunger.

19. A pycnometer apparatus comprising:
- a block of highly thermally conductive material;
- a sample chamber bored into the center of said block and defining an opening of said sample chamber communicating with the exterior of said block;
- an expansion chamber bored into the center of said block and connected by a first passageway to said sample chamber, said expansion chamber positioned in close proximity to said sample chamber;
- means for selectively closing said opening so as to define an identical volume within said sample chamber each time said sample chamber is closed;
- gas supply means for introducing a gas under pressure through an inlet valve into said sample chamber through a second passageway;
- expansion valve means for controlling flow of gas through said first passageway;
- vent means connected to said expansion chamber by a third passageway for venting said expansion chamber to atmosphere;
- means connected to said sample chamber by a fourth passageway for measuring pressure within said sample chamber; and
- purging control means for:
  - (a) opening said expansion valve means;
  - (b) operating said gas supply means to open said inlet valve and pressurize said sample chamber and said expansion chamber with a gas to a pressure above atmospheric pressure;
  - (c) closing said inlet valve after pressurization of said chambers;
  - (d) waiting for a predetermined period of time;
  - (e) opening said vent means to allow said gas to expand to atmosphere;
  - (f) repeating functions (b) through (e);
- said passageways being located in the interior of said block.

20. The apparatus of claim 19, wherein said means for defining an identical volume comprises:
- an annular surface surrounding said opening defined by said sample chamber;
- a cap including a mating surface, said mating surface engaging said annular surface to define said fixed volume when said cap is in a sealing position with respect to said opening;
- a compressible gasket member mounted in said cap such that said gasket member is compressed in sealing relationship against said annular surface when said cap is in said sealing position; and means for selectively retaining said cap in said sealing position.

21. The apparatus of claim 19, wherein said means for defining an identical volume comprises:

a continuous surface defined in said block surrounding said opening defined by said sample chamber;

a cap including a rigid portion engaging said block to define said fixed volume when said cap is in a sealing position with respect to said opening;

a compressible gasket member mounted in said cap such that said gasket member is compressed in sealing relationship against said continuous surface when said cap is in said sealing position; and means for selectively retaining said cap in said sealing position.

22. The apparatus of claim 21, wherein said cap comprises:

a body;

a plunger mounted for movement with respect to said body, said plunger defining said rigid portion and carrying said gasket member; and means for urging said plunger away from said body such that when said cap is in said sealing position, said plunger engages said continuous surface and said gasket is compressed.

23. The apparatus of claim 22, wherein said rigid portion defined by said plunger comprises an annular projection shaped to be matingly received by said continuous surface; and said gasket member comprises an O-ring received in a groove defined in said annular projection.

24. The apparatus of claim 22, wherein said means for selectively retaining said cap in said sealing position engages said body while permitting movement of said plunger.

25. The apparatus of claim 19 wherein said material of high thermal conductivity comprises aluminum.

26. The apparatus of claim 19 wherein said gas supply means admits said gas into said sample chamber to establish a predetermined fill pressure within a predetermined tolerance of said fill pressure.

27. A pycnometer apparatus, comprising:

a sample chamber;

an expansion chamber connected by a passageway to said sample chamber, said sample and expansion chambers being positioned within an integral environment of high thermal conductivity;

gas supply means for introducing a gas under pressure into one of said chambers;

valve means for controlling flow of gas through said passageway;

vent means for venting either of said chambers to atmosphere; and means for measuring the pressure of gas within said one of said chambers.

28. A pycnometer apparatus, comprising:

a sample chamber defining a sample loading opening;

an expansion chamber connected by a passageway to said sample chamber, said sample and expansion chambers being positioned adjacent to one another within an integral environment of high thermal conductivity;

means for selectively closing said sample loading opening so as to define an identical volume within said sample chamber each time said sample chamber is closed;

gas supply means for introducing a gas under pressure into one of said chambers;

valve means for controlling flow of gas through said passageway;

vent means for venting either of said chambers to atmosphere;

means for measuring the pressure of gas within said one of said chambers; and purging means for repeatedly pressurizing said chambers with a purging gas;

said passageway being located essentially entirely within said environment.

29. The apparatus of claim 28, wherein said gas supply means admits said gas into said one chamber to within a desired tolerance of a predetermined fill pressure.

* * * * *

REEXAMINATION CERTIFICATE (3537th)

United States Patent [19]
Orr et al.

[11] B1 5,074,146
[45] Certificate Issued Jun. 9, 1998

[54] GAS COMPARISON PYCNOMETER

[75] Inventors: Clyde Orr, Dunwoody; Ronnie W. Camp, Duluth; Kathryn H. Gibson, Stone Mountain, all of Ga.

[73] Assignee: Micromeritics Instrument Corporation, Norcross, Ga.

Reexamination Request:
No. 90/004,498, Dec. 26, 1996

Reexamination Certificate for:
Patent No.: 5,074,146
Issued: Dec. 24, 1991
Appl. No.: 438,752
Filed: Nov. 17, 1989

[51] Int. Cl.$^6$ .................... G01N 9/00; G01N 9/26; G01F 17/00
[52] U.S. Cl. .................... 73/149; 73/32 R; 73/37; 364/564
[58] Field of Search .................... 73/37, 149, 290 B, 73/32 R, 434; 364/558, 564

[56] References Cited

U.S. PATENT DOCUMENTS

| | | | |
|---|---|---|---|
| 1,885,926 | 11/1932 | Lewis | 73/290 B |
| 2,304,731 | 12/1942 | Fairbairn | |
| 2,667,782 | 2/1954 | Shea | 73/149 |
| 3,060,724 | 10/1962 | Smith, Jr. et al. | 73/149 |
| 3,113,448 | 12/1963 | Hardway, Jr. et al. | 73/149 X |
| 3,255,122 | 6/1966 | Constabaris et al. | 73/38 |
| 3,788,125 | 1/1974 | Kirschstein et al. | 73/32 R |
| 3,895,519 | 7/1975 | Bouchy et al. | 73/149 |
| 4,083,228 | 4/1978 | Turner et al. | 73/32 R |
| 4,095,473 | 6/1978 | Batchelor et al. | 73/433 |
| 4,112,738 | 9/1978 | Turner | 73/149 X |
| 4,239,623 | 12/1980 | Schrenker | |
| 4,391,141 | 7/1983 | Petersen | 73/149 X |
| 4,527,418 | 7/1985 | Arcara | 73/32 R X |
| 4,640,122 | 2/1987 | Héraud et al. | 73/149 X |
| 4,763,518 | 8/1988 | Daviaud et al. | 73/149 |
| 4,770,033 | 9/1988 | Nicolai | 73/149 |
| 4,972,730 | 11/1990 | Camp et al. | 73/865.5 |

FOREIGN PATENT DOCUMENTS

| | | |
|---|---|---|
| 31985 | 3/1980 | Japan |
| 20814 | 2/1984 | Japan |
| 108231 | 5/1988 | Japan |
| 246620 | 10/1988 | Japan |

OTHER PUBLICATIONS

Shell Method Series (666/49U) "Determination of Surface Properties Of Porous Solids Low Temperature Nitrogen Adsorption Method"—1949, pp. 1–7.

"Model 6102—Gas Comparison Pycnometer" Systems Science and Software at Pittsburgh Conference May 1978 4 pages.

"A Microprocessor Controlled Gas Pycnometer" by Ronnie Camp et al. pp. 1–9 by Mar. 1980.

"Micromeritics Auto Pycnometer 1320" 4 pages by Micromeritics Corporation by about Jun. 1989.

1 page drawing revision for Autopycnometer 1320 entitled "Assy, Sample Knob" dated Jun. 24, 1982.

Hillar M. Rootare et al. "Effect of Adsorbed Water on Sample Surface Density Measurement with an Automatic Helium Pycnometer", Abstract No. 908, 1 page, Pittsburgh Conference on Analytical Chemistry and Applied Spectroscopy Mar. 1981.

Ronnie W. Camp et al. A Microprocessor Controlled Gas Pycnometer, Abstract No. 288, 1 page Pittsburgh Conference on Analytical Chemistry and Applied Spectroscopy held Mar. 10–14, 1980 Atlantic City, NJ.

(List continued on next page.)

*Primary Examiner*—Thomas P. Noland

[57] ABSTRACT

A gas comparison pycnometer is disclosed which provides a method and apparatus for determining and checking the accuracy of the volume of a solid substance. The pycnometer is also outfitted with a unique cap assembly which fixes the volume in the pycnometer's sample chamber from run to run. The pycnometer also employs a series of purges with a suitable gas to carry unwanted moisture and vapors out of the system. This pycnometer solves many problems in the prior art by quickly and accurately determining the volume of a solid substance.

OTHER PUBLICATIONS

"Multivolume Pycnometer 1305", 2 pages, Micromeritics, Corporation by Jan. 1987.

"Instruction Manual Multivolume Pycnometer 1305" Jan. 23, 1987, 6 beginning pages, pp. 1–1 to A–9, 2 end pages. 1 page drawing revision for Multivolume Pycnometer entitled "Cop. Sample Chamber" dated May 13, 1981.

Shibata Brochure Analysis Prepared for Micromeritics Instrument Corp. Surface Area Apparatuses, Type ASA—2000, pp. 1–7, published 6, Jul. 1990.

Lagus, Turner and Gaffney, "A Rapid, Accurate Technique for Determining Densities of High Explosives", 1977, p. 82 of Propellants and Explosives 2, 81–84 (1977).

International Standard—ISO–4590—1981 (E), "Cellular plastics—Determination of volume percentage of open and closed cells of rigid materials", Dec. 1981, 9 pages.

Quantachrome Corporation, "Steropycnometer", SPY–2 (Operator's Manual), Mar. 1982, pp. 1–18.

Micromeritics Instrument Corporation, "Instruction Manual Autopycnometer 1320", 28 Feb. 1985, cover page+8 pages+ pp. 1–1 to 6–1 & A1–A4.

ASTM Designation: C604–86, "Standard Test Method for True Specific Gravity of Refractory Materials by Gas–Comparison Pycnometer", Sep. 1986 pp. 1–3.

Quantachrome Corporation "Penta–Pycnometer Model PP–4" (Operator's Manual), Mar. 1987, pp. I–4A, II–1, –2, III–1–2A, IV–1–17, V–1–9, and VI–1–2 and VII–1–3.

Horiba, "Helium Pycnometer VM–100", Bulletin: HRE–8815A, 1988, 2 pages. (date provided by requester).

ބ1 5,074,146

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 19–29 is confirmed.

Claims 1–3 and 8 are determined to be patentable as amended.

Claims 4–7 and 9–18, dependent on an amended claim, are determined to be patentable.

New claims 30 and 31 are added and determined to be patentable.

1. An apparatus for determining the volume of a solid substance comprising:

a sample chamber containing said substance;

an integral expansion chamber connected by a passageway to said sample chamber, *said sample and expansion chambers being positioned in an integral environment of high thermal conductivity*;

gas supply means for introducing a gas under pressure into one of said chambers;

valve means for controlling flow of gas through said passageway;

vent means for venting either of said chambers to atmosphere;

means for measuring the pressure of gas within said one of said chambers; and control means for:
   (a) operating said gas supply means to pressurize with a gas the one of said chambers containing said pressure measuring means;
   (b) operating said pressure measuring means to measure the pressure in said one chamber;
   (c) operating said valve means to allow expansion of said gas through said passageway into said other chamber;
   (d) operating said pressure measuring means to measure the pressure in said connected chambers;
   (e) calculating a first volume of said sample;
   (f) storing said first volume;
   (g) operating said vent means to vent said chambers to atmosphere;
   (h) repeating (a) through (d);
   (i) calculating an additional volume of said sample;
   (j) comparing two or more of said volumes;
   (k) responsive to said compared volumes being within a predetermined tolerance, accepting one of said compared volumes as the volume of said sample; and
   (l) responsive to said compared volumes being outside said predetermined tolerance repeating steps (h)–(j) until said compared volumes are within said predetermined tolerance.

2. A method for determining the volume of a solid substance contained in a sample chamber of a pycnometer having an integral expansion chamber and a passageway connecting said chambers, *said sample and expansion chambers being positioned in an integral environment of high thermal conductivity*, comprising the steps of:
   (a) pressurizing one of said chambers with a gas;
   (b) measuring the pressure in said pressurized chamber;
   (c) allowing expansion of said gas into said other chamber;
   (d) measuring the pressure in said connected chambers;
   (e) calculating a first volume;
   (f) storing said first volume;
   (g) venting said chambers to atmosphere;
   (h) repeating (a) through (d);
   (i) calculating an additional volume of said sample;
   (j) comparing two or more of said volumes;
   (k) accepting one of said compared volumes as the volume of said sample if said compared volumes are within a predetermined tolerance; and
   (l) repeating steps (h) through (j) if said compared volumes are outside said predetermined tolerance, until said compared volumes are within said tolerance.

3. A pycnometer apparatus comprising:

a sample chamber containing a substance;

an integral expansion chamber connected by a passageway to said sample chamber, *said sample and expansion chambers being positioned in an integral environment of high thermal conductivity*;

gas supply means for introducing a gas under pressure into one of said chambers through a gas supply valve;

expansion valve means for controlling flow of gas through said passageway;

vent valve means for venting either of said chambers to atmosphere;

means for measuring the pressure of gas within said one of said chambers; and control means for:
   (a) operating said supply valve so as to admit gas into said one chamber until the pressure within said one chamber approaches a predetermined fill pressure in said one chamber within a predetermined tolerance of said fill pressure;
   (b) closing said supply valve;
   (c) operating said pressure measuring means;
   (d) generating an error signal if the pressure in said one chamber exceeds said fill pressure by more than said tolerance;
   (e) momentarily admitting additional gas if the pressure in said one chamber is lower than said fill pressure by more than said tolerance;
   (f) repeating functions (b) through (e) until the pressure in said one chamber is within said tolerance; and
   (g) operating said expansion valve means to allow expansion of said gas through said passageway into said other chamber.

8. A method for determining the volume of a substance contained in a sample chamber of a pycnometer having an integral expansion chamber and a passageway connecting said chambers, *said sample and expansion chambers being positioned in an integral environment of high thermal conductivity*, comprising the steps of:
   (a) pressurizing one of said chambers with a gas to establish a predetermined fill pressure in said one chamber within a predetermined tolerance of said fill pressure;
   (b) admitting said gas until the pressure in said one chamber approaches said predetermined fill pressure;

(c) measuring the pressure in said one chamber;

(d) generating an error signal if the pressure in said one chamber exceeds said fill pressure by more than said tolerance;

(e) momentarily admitting additional gas if the pressure in said one chamber is lower than said fill pressure by more than said tolerance;

(f) repeating steps (b) through (e) until the pressure in said one chamber is within said tolerance;

(g) allowing expansion of said gas into said other chamber;

(h) measuring the pressure in said connected chambers;

(i) calculating the volume of said substance.

30. A pycnometer apparatus comprising:

a block of highly thermally conductive material;

a sample chamber formed in said block and defining an opening of said sample chamber communicating with the exterior of said block;

an expansion chamber formed in said block and connected by a first passageway via an expansion valve to said sample chamber, said expansion chamber positioned in close proximity to said sample chamber;

a cap closing said opening so as to define an identical volume within said sample chamber each time said sample chamber is closed;

a source of gas under pressure connected to one of said chambers for introducing such gas thereinto through a second passageway via an inlet valve;

vent means for venting either of said chambers to atmosphere, said vent means including a third passageway connecting one of said chambers to a vent to atmosphere; and a pressure transducer connected to one of said chambers by a fourth passageway for measuring the pressure of gas within said one of said chambers.

31. A pycnometer apparatus comprising:

a block of highly thermally conductive material;

a sample chamber formed in said block and defining an opening of said sample chamber communicating with the exterior of said block;

a cap closing said opening;

an expansion chamber formed in said block and connected by a passageway via an expansion valve to said sample chamber, said expansion chamber positioned in close proximity to said sample chamber;

a source of gas under pressure connected to one of said chambers for introducing such gas thereinto via an inlet valve;

vent means for venting either of said chambers to atmosphere; and a pressure transducer connected to one of said chambers for measuring the pressure of gas within said one of said chambers.

* * * * *